United States Patent [19]

Hilverda

[11] Patent Number: Plant 7,459

[45] Date of Patent: Feb. 26, 1991

[54] CARNATION NAMED HILSTEFA

[75] Inventor: Jan J. Hilverda, Aalsmeer, Netherlands

[73] Assignee: Hilverda b.v., Netherlands

[21] Appl. No.: 299,773

[22] Filed: Jan. 23, 1989

[51] Int. Cl.[5] ..... A01H 5/00

[52] U.S. Cl. ..... Plt./71

[58] Field of Search ..... Plt./70, 71, 73

*Primary Examiner*—James R. Feyrer

*Attorney, Agent, or Firm*—Charles W. Rummler

[57] ABSTRACT

A new spray carnation cultivar particularly distinguished by its profuse production of rather small flowers having a dark pink coloration of the inside surface of the flower petals which is enlivened by white edges, the reverse side of the petals being white, the flowers being borne in a cluster at the upper end of a long, strong flower stem. The plant itself is a tall bush having a height of about 100 cm. with a rapid, vigorous and upright growth habit and abundant foliage.

1 Drawing Sheet

BACKGROUND OF THE NEW PLANT

This new spray carnation cultivar originated as a seedling of a hybrid plant resulting from my crossing of selected varieties of stock plants maintained by me in my nursery at Aalsmeer, The Netherlands, for breeding purposes. The present plant was selected by me for propagation, from among the seedlings grown from seeds of the original hybrid, because of its very unusual flower coloration and its profuse production of flowers borne on long, strong flowering stems. Propagation of the selected seedling was done under my direction at Aalsmeer, The Netherlands, by means of cuttings. The results of that propagation were so pleasing that propagation was continued at Aalsmeer through several successive generations, which demonstrated conclusively that the distinguishing characteristics of this new variety would hold true from generation to generation and that its homogeneity could be assured for commercial propagation for the production of cut flowers. Propagation of this new carnation variety by means of cuttings is now being done at Aalsmeer, The Netherlands, for commercial purposes.

DESCRIPTION OF THE DRAWING

My new spray carnation cultivar is illustrated by the accompanying photographic drawing which shows, in full color, a flower stem with several buds and mature flowers, a full face view of one of the flowers, and views showing a partially opened bud and a pair of flower petals, the colors shown being as nearly true as it is reasonably possible to obtain by conventional photographic procedures.

DESCRIPTION OF THE NEW PLANT

The following is a detailed description of my new spray carnation cultivar based upon observations during the summer of 1988 at Aalsmeer, The Netherlands, the color designations being according to The R.H.S. Colour Chart published by The Royal Horticultural Society of London, England.

THE PLANT

Origin: Seedling.

Parentage:

*Seed parent.*—An unnamed and unpatented variety of carnation.

*Pollen parent.*—An unnamed and unpatented carnation variety.

Both varieties having been selected by me from my collection of carnation varieties maintained at my nursery in Aalsmeer, The Netherlands, for breeding purposes.

Classification:

*Botanic.*—*Dianthus caryophyllus* L.

*Commercial.*—Spray Carnation.

Form: Tall, erect bush comprising a plurality of stems emitted near the ground.

Height: About 100 cm.

Growth habit: Rapid, strong, vigorous and upright.

Foliage:

*Quantity.*—Abundant.

*Size of leaf.*—About 12 to 13 cm. long.

*Leaf shape.*—Elliptic with entire margins.

*Texture.*—Leathery.

*Color.*—Upper side and under side, Blue Green.

*Ribs and veins.*—Prominent midrib.

THE BUD

Size: Medium.

*Diameter.*—About 12 to 15 mm.

*Length.*—About 20 to 22 mm.

Form: Cylindrical.

Rate of opening: With a mature bud, the flower petals appear in approximately five days.

Color of petals: When sepals first divide, Dark Pink. When petals being to unfurl, Dark Pink.

Sepals:

*Number.*—Five.

*Character.*—Hooded over the bud before dividing and standing up when the flower opens.

*Color.*—Inside, Light Green. Outside, Dark Green.

*Striae.*—Very thin and of Light Green to Yellowish color.

Calyx:

*Shape.*—Cylindrical.

*Size.*—Medium.

*Splitting.*—The calyx does not split.

*Aspect.*—Smooth.

Flower stem:

*Length.*—About 60 cm., in average.

*Character.*—Rigid and erect.

*Color.*—Dark Green.

THE FLOWER

Blooming habit: Continuous and profusely.
Flower size: Small.
*Diameter.*—About 45 mm.
*Depth.*—About 20 mm.
Borne: On a long, strong stem of more than three flowers per stem.
Shape: When bloom first opens, high centered. When bloom matures, it flattens.
Petalage:
*Number of petals.*—Averages about 30 to 34.
*Arrangement.*—Imbricated.
*Form.*—Fan-shaped with crenate margin and acute apex.
*Texture.*—Soft.
*Aspect.*—Velvety.
*Color.*—Inner side of petals, Dark Pink, approximately RHS 62-A. The exact color of this flower cannot be found in the RHS Color Charts. However, Dutch breeder's rights were obtained in 1986 and in their official report, the authorities then described the color as follows: Petal — Main Color, approximately RHS 62-A, but somewhat lighter, easily fading to approximately RHS 62-C. Thin white stripes occasionally found.
Flower stem:
*Length.*—Averages about 60 cm.
*Color.*—Dark Green.
*Character.*—Sturdy and upright.
Discoloration after full bloom: Slight fading does occur but only after three days exposure of the fully opened flower to bright daylight conditions.
Persistence: The flowers hang on and dry.

Disease resistance: Resistant to *Fusarium oxysporum* as observed in practive growing in The Netherlands.
Fragrance: Weak.
Lasting quality: As a cut flower, ten to fourteen days.

REPRODUCTIVE ORGANS

Stamens:
*Number.*—12 to 14 uniformly arranged around the ovary.
*Anthers.*—Size: Normal. Color: Cream White.
*Filaments.*—Length: About 20 mm. Color: White.
*Pollen.*—Color: White.
Pistils:
*Number.*—One.
*Styles.*—Length: About 20 mm. Color: White.
*Stigmas.*—Color: White.

THE FRUIT

Fertility: The fruit is fertile.
Shape: Lozenge-shaped.
Color at maturity: Yellow/Brown.

This new spray carnation variety most nearly resembles the variety 'Silvery Pink' (unpatented). This new variety is distinguished from 'Silvery Pink', however, by its darker pink color, more flowers buds per stem, and higher production.

I claim:

1. The new and distinct spray carnation cultivar substantially as herein shown and described, characterized by its relatively small flowers each having about thirty to thirty-four petals, the inner side of which have a dark pink coloration, the flowers being produced profusely on long, rigid and erect stems of a tall, strong plant having a vigorous and upright growth habit and abundant foliage.

* * * * *

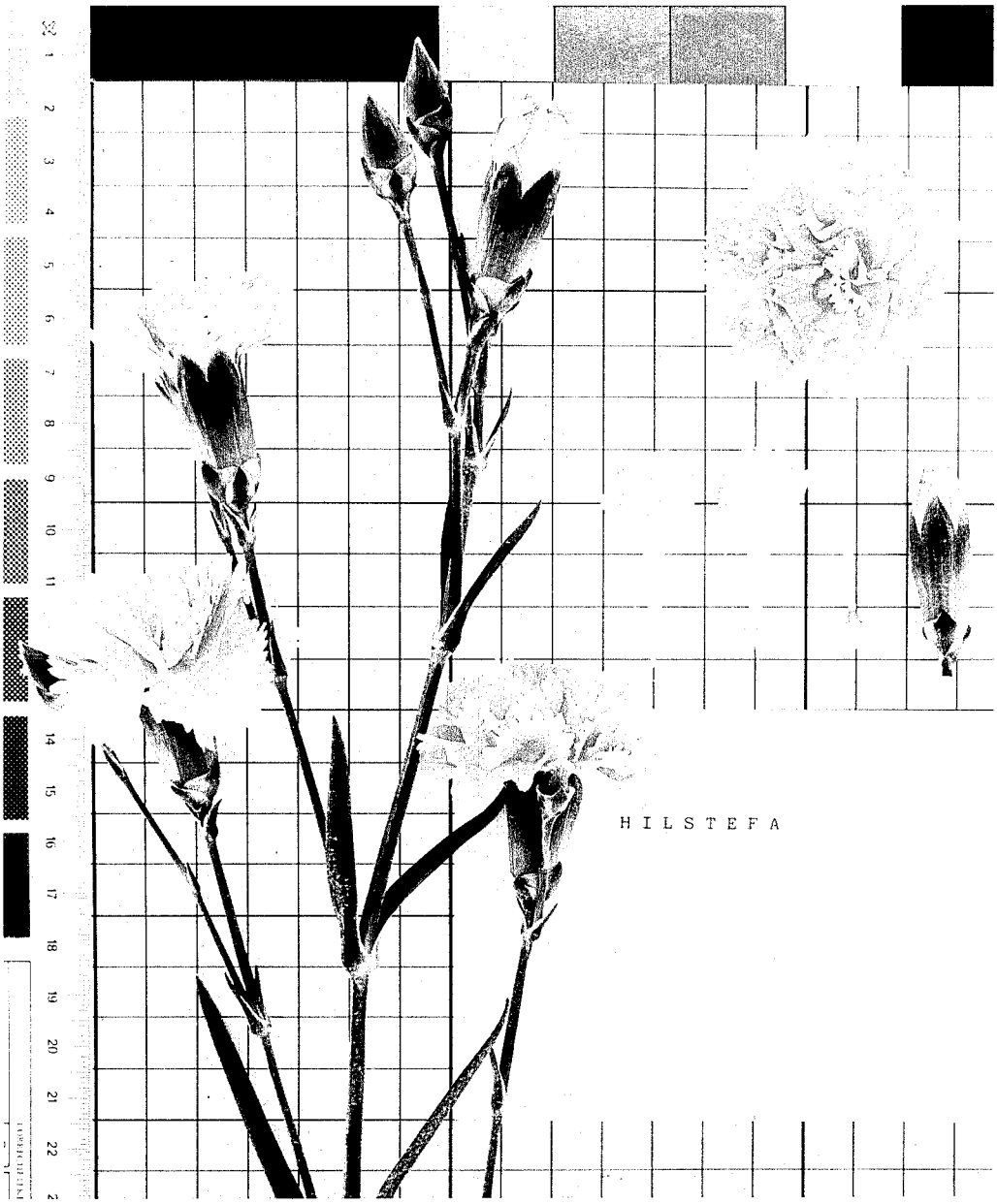
HILSTEFA